United States Patent [19]
Klimisch

[11] Patent Number: 5,280,019
[45] Date of Patent: Jan. 18, 1994

[54] SKIN TREATMENT WITH CARBOXYFUNCTIONAL SILOXANES

[75] Inventor: Helen M. Klimisch, Midland, Mich.

[73] Assignee: Dow Corning Corporation, Midland, Mich.

[21] Appl. No.: 683,631

[22] Filed: Apr. 11, 1991

Related U.S. Application Data

[63] Continuation-in-part of Ser. No. 488,159, Mar. 5, 1990, abandoned.

[51] Int. Cl.$^5$ .............................. A61K 31/695
[52] U.S. Cl. ................................ 514/63; 514/873
[58] Field of Search .................. 424/723; 514/63, 873

[56] References Cited

U.S. PATENT DOCUMENTS

| | | | |
|---|---|---|---|
| 3,818,105 | 6/1974 | Coopersmith et al. | 424/358 |
| 3,852,075 | 12/1974 | Basadur | 106/11 |
| 4,113,677 | 9/1978 | Svedas et al. | 260/23 R |
| 4,246,285 | 1/1981 | Van Duzee | 424/358 |
| 4,271,215 | 6/1981 | Coon | 427/387 |
| 4,477,514 | 10/1984 | Gee et al. | 428/264 |
| 4,559,227 | 12/1985 | Chandra et al. | 424/70 |
| 4,563,347 | 1/1986 | Starch | 424/70 |
| 4,749,732 | 6/1988 | Kohl et al. | 524/43 |
| 4,810,253 | 3/1989 | Kasprzak et al. | 8/137 |
| 4,844,888 | 7/1989 | Zawadzki | 429/69 |
| 4,848,981 | 7/1989 | Kasprzak et al. | 8/137 |
| 4,857,212 | 8/1989 | Ona et al. | 252/8.6 |

*Primary Examiner*—Frederick E. Waddell
*Assistant Examiner*—M. Moezie
*Attorney, Agent, or Firm*—Timothy J. Troy

[57] ABSTRACT

A method of treating human skin to enhance the ability of skin in the absorption and retention of moisture in order to retard skin moisture loss. There is applied to skin an organosilicon compound exhibiting humectant-like characteristics which is a carboxylic acid salt functional polysiloxane. An alternate method treats human skin to reduce the transepidermal water loss of skin in order to enhance skin softness. There is applied to skin an occlusive film forming organosilicon compound which is a carboxyfunctional polysiloxane or its metal carboxylate salt.

17 Claims, No Drawings

SKIN TREATMENT WITH CARBOXYFUNCTIONAL SILOXANES

RELATED APPLICATIONS

This application is a continuation-in-part of my prior copending application Ser. No. 07/488,159 filed Mar. 5, 1990 and entitled "Emollient Durability Enhancing Siloxanes", now abandoned.

BACKGROUND OF THE INVENTION

This invention relates to the treatment of human skin with certain organosilicon compounds which are carboxyfunctional and carboxylic acid salt functional polysiloxanes.

Mineral oil is a highly refined, colorless, tasteless, and odorless liquid mixture of hydrocarbons obtained from petroleum that has been used medicinally as an internal lubricant and in the manufacture of various salves and ointments. It is also known as medicinal oil, white mineral oil, heavy mineral oil, light mineral oil, liquid paraffin and paraffin oil. Mineral oil has long been the emollient of choice in creams and lotions. It is second only to water as a moisturizer ingredient. Mineral oil acts as a moisturizer primarily through the functioning of the ingredient as an occlusive barrier. The water content of the outer layers of the stratum corneum of the human skin is a controlling factor in the appearance of dry skin symptoms. When the stratum corneum contains an adequate amount of water within the range of ten to twenty percent the skin remains flexible. However, when the water content falls below ten percent the stratum corneum often becomes brittle and rough and can exhibit scaling and cracking.

The stratum corneum receives its water from the deep layers of the epidermis by diffusion or when it is brought into direct contact with water. The diffusion process is controlled by the water content of the skin as well as the concentration gradient. In a very dry environment, the water loss from the external skin layers can be significant and often exceeds the rate of replacement by diffusion. An occlusive barrier of mineral oil placed onto the surface of the skin acts to retard the water loss to the environment and allows the skin surface to rehydrate by the diffusion process. Due to the effectiveness, low cost, and safety of petroleum derivatives such as mineral oil, it serves as a useful occlusive moisturizer and contributes to dry skin prevention by protection and moisture retention, as well as dry skin repair by emolliency, lubricity and moisture restoration.

While mineral oil has been found to be an effective and economical emollient for skin care applications and provides softening, smoothing and a protective action on skin, it nevertheless suffers from the disadvantage that it is easily removed from the skin by washing the skin with soap. Thus the effectiveness and long term benefits of mineral oil enumerated above are of a limited duration. However in accordance with the present invention, it has been discovered that certain carboxyfunctional organosilicon compounds act as durability enhancers when mixed with mineral oil and provide skin care formulations that a consumer can perceive as being longer lasting and more aesthetically pleasing.

It is not new to employ mineral oil in skin conditioning formulations. For example this is clearly taught in U.S. Pat. No. 3,818,105 issued Jun. 18, 1974, and in U.S. Pat. No. 4,246,285 issued Jan. 20, 1981. Aminofunctional, amidofunctional and carboxyfunctional organosilicon compounds are not new and such siloxanes are shown in U.S. Pat. No. 4,271,215 issued Jun. 2, 1981; U.S. Pat. No. 4,477,514 issued Oct. 16, 1984; U.S. Pat. No. 4,559,227 issued Dec. 17, 1985; U.S. Pat. No. 4,563,347 issued Jan. 7, 1986; U.S. Pat. No. 4,749,732, issued Jun. 7, 1988; U.S. Pat. No. 4,810,253 issued Mar. 7, 1989; U.S. Pat. No. 4,848,981 issued Jul. 18, 1989; and in U.S. Pat. No. 4,857,212 issued Aug. 15, 1989. However none of these references teach the combination of mineral oil with such siloxanes and there use on the skin as durability enhancers. Formulations containing mineral oil and an aminofunctional siloxane are know as exemplified by U.S. Pat. No. 3,852,075 issued Dec. 3, 1974 and U.S. Pat. No. 4,113,677 issued Sep. 12, 1978 but such formulations are employed to clean and polish automotive vehicles rather than as personal skin care applications.

SUMMARY OF THE INVENTION

This invention relates to a method of treating human skin to enhance the ability of skin in the absorption and retention of moisture in order to retard skin moisture loss. In accordance with the invention there is applied to skin an organosilicon compound exhibiting humectant-like characteristics. The organosilicon compound is a carboxylic acid salt functional polysiloxane.

The invention is also directed to a method of treating human skin to reduce the transepidermal water loss of skin in order to enhance skin softness. In this embodiment of the invention there is applied to skin an occlusive film forming organosilicon compound. The organosilicon compound is either a carboxyfunctional or carboxylic acid salt functional polysiloxane.

The invention further relates to a skin conditioning composition of enhanced durability which is a mixture of an emollient material and an effective amount of an organosilicon compound. The organosilicon compound can be either an aminofunctional, amidofunctional or carboxyfunctional polysiloxane.

These and other features, objects and advantages of the herein described present invention will become more apparent from a consideration of the following detailed description thereof.

DETAILED DESCRIPTION OF THE INVENTION

In accordance with the present invention, there is provided a concept which relates to the enhancement of the DC 3563 durability of emollient materials with certain organosilicon compounds. The durability on human skin is enhanced by mixing an emollient with either one of an aminofunctional, amidofunctional or carboxyfunctional polysiloxane. These aminofunctional, amidofunctional and carboxyfunctional organosilicon compounds are well known in the prior art, and such compounds as well as methods for preparing these compounds can be found in U.S. Pat. No. 4,477,514, issued Oct. 16, 1984, which shows carboxyfunctional siloxanes; U.S. Pat. No. 4,559,227 issued Dec. 17, 1985 which shows aminofunctional siloxanes; and U.S. Pat. No. 4,848,981 issued Jul. 18, 1989 which shows the amidofunctional siloxanes of the present invention. These patents are considered incorporated herein by reference.

The amine functional siloxane polymer has the formula $$R_{3-z'}Q_zSiO[R_2'SiO]_x[R'QSiO]_ySiQ_zR_{3-z'}$$

wherein R' denotes an alkyl group of 1 to 4 carbons or a phenyl group with the proviso that at least 50 percent of the total R' groups are methyl; Q denotes an amine functional substituent of the formula —R"Z wherein R" is a divalent alkylene radical of 3 to 6 carbon atoms or a radical of the formulation —CH$_2$CH$_2$CH$_2$OCH$_2$—CHOHCH$_2$— and Z is a monovalent radical selected from the group consisting of —NR$_2$''', —NR''''(CH$_2$)$_n$NR$_2$'''; and $$\underset{\underset{X'}{|}\qquad\underset{X}{|}}{NR'''(CH_2)_nN(R''')\overset{O}{\overset{\|}{C}}R'''}$$

wherein R''' denotes hydrogen or an alkyl group of 1 to 4 carbons, R'''' denotes an alkyl group of 1 to 4 carbons and n is a positive integer from 2 to 6; z has a value of 0 or 1; x has an average value of 25 to 3000; y has an average value of 0 to 100 when z is 1, and y has an average value of 1 to 100 when z is 0.

The amidofunctional polysiloxane is a triorganosiloxane- endblocked polydiorganosiloxane having an average of 50 to 1000 siloxane units per molecule with an average of 1 to 50 of the siloxane unites per molecule being amide-containing siloxane units. The amide-containing siloxane units bear a substituent of the formula $$\underset{\underset{X'}{|}\qquad\underset{X}{|}}{-R'(NCH_2CH_2)_nNR''}$$

wherein n is 0 or 1; R' denotes an alkylene radical of 3 to 6 carbon atoms; R" denotes a hydrogen radical or an alkyl radical of 1 to 6 carbon atoms; X denotes an acyl radical of the formula $$-\overset{O}{\overset{\|}{C}}R''',$$

X' denotes a hydrogen radical or X; and R''' denotes an alkyl radical of 1 to 4 carbon atoms; substantially all other organic substituents in the polydiorganosiloxane being methyl groups.

The amidofunctional silicone consists essentially of a triorganosiloxane-endblocked polydiorganosiloxane which contains amidoalkyl substituents. Triorganosiloxane- endblocked polydiorganosiloxanes or amidofunctional silicones consist essentially of terminal triorganosiloxane units of the formula R$_3$SiO$_{\frac{1}{2}}$ and backbone diorganosiloxane units of the formula R$_2$SiO$_{2/2}$. Trace amounts of other siloxane units in the amidofunctional silicone such as SiO$_{4/2}$ and RSiO$_{3/2}$ which are impurities in commercial polydiorganosiloxanes may be present. Preferably there are no SiO$_{4/2}$ units or RSiO$_{3/2}$ units in the amidofunctional silicones.

The R radicals of the above siloxane units are substantially either amide-containing radicals of the formula $$\underset{\underset{X'}{|}\qquad\underset{X}{|}}{-R'(NCH_2CH_2)_nNR''}$$

or methyl radicals. Minor amounts of other organic substituents which are impurities in commercial polydiorganosiloxanes may be present. It should be understood that the amidofunctional silicones are sometime prepared by acylation of corresponding aminofunctional silicones. Consequently the amidofunctional silicones may also contain residual aminofunctional siloxane units. For example siloxane units such as H$_2$NCH$_2$CH$_2$NHCH$_2$CH(CH$_3$)CH$_2$SiO$_{2/2}$ or H$_2$NCH$_2$CH$_2$CH$_2$SiO$_{2/2}$ may be present. It is preferred to employ silicone oils that do not contain levels of more than 25 percent of the number of amidofunctional substituents of the unmodified aminofunctional siloxane units.

In the formula for the amide-containing radicals R' denotes an alkylene radical of 3 to 6 carbon atoms such as —CH$_2$CH$_2$CH$_2$—, —CH$_2$CH$_2$CH$_2$CH$_2$—, —CH$_2$CH(CH$_3$)CH$_2$—, —CH$_2$CH$_2$CH$_2$CH$_2$CH$_2$— and —CH$_2$CH(CH$_2$CH$_3$)CH$_2$—. Amidofunctional silicones wherein the silicon bonded amide-containing radicals have a trimethylene radical or an alkylated trimethylene radical such as —CH$_2$CH(CH$_3$)CH$_2$— as the R' radical are preferred. R" denotes a hydrogen radical which is a preferred R" radical or an alkyl radical of 1 to 6 carbon atoms such as methyl, ethyl, propyl, butyl, and isobutyl.

In the formula for the amide-containing radicals n has a value of 0 or 1 so that the radical may contain one or two nitrogen atoms. X denotes an acyl radical of the formula $$-\overset{O}{\overset{\|}{C}}R'''$$

and X' denotes a hydrogen radical or X. In the acyl radical R''' denotes an alkyl radical of 1 to 4 carbon atoms such as methyl, ethyl, propyl, isopropyl or butyl.

Triorganosiloxane-endblocked polydiorganosiloxanes preferred consist essentially of siloxane units such as

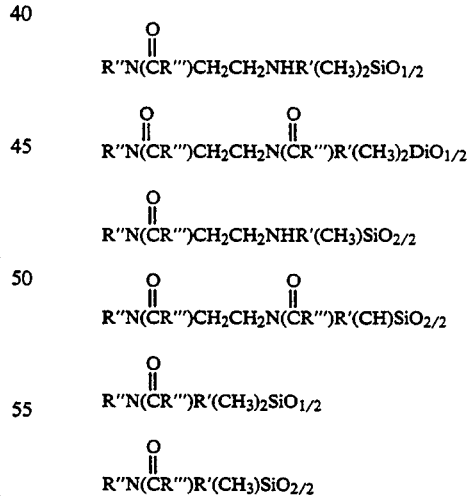

(CH$_3$)$_3$SiO$_{\frac{1}{2}}$ and (CH$_3$)$_2$SiO$_{2/2}$ where R', R" and R''' have the same meanings as described above. It should be understood that any of the siloxane units having non-acylated nitrogen atoms can also be present in their salt form. It is well known that the salt form occurs when such polymers are neutralized by acids such as mineral acids or carboxylic acids.

The silicone polymers may contain amide-containing siloxane units of the formula

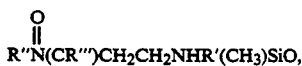

wherein R', R" and R'" have the same meanings as described above. These amide-containing units have a ratio of acyl groups to nitrogen atoms of about 0.5.

The carboxyfunctional silicones of the invention have the formula

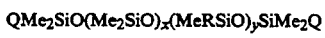

wherein Me is a methyl radical; R is a carboxyfunctional radical; the carboxyfunctional radical being selected from the group consisting of carboxyalkyl radicals and carboxythioalkyl radicals; Q is selected from the group consisting of R, Me and OH groups; x has a value of 1 to 1000; and y has a value of 1 to 100.

As referred to herein, a carboxyfunctional radical is a monovalent radical which contains the —COOH radical, and is attached to a silicon atom of the main molecular chain by a divalent linking group. Direct attachment to the silicon atom is through a silicon to carbon bond.

Divalent linking groups contemplated for use in the present invention are either alkylene groups containing from 2 to 10 carbon atoms or thioalkylene groups containing 2 to 9 carbon atoms and one sulfur atom present as a thioether group. Carboxyfunctional radicals wherein the divalent linking group is an alkylene group are referred to herein as carboxyalkyl radicals; carboxyfunctional radicals wherein the divalent linking group is a thioalkylene group are referred to herein as carboxythioalkyl radicals.

Examples of carboxyalkyl radicals include but are not limited to —CH$_2$CH$_2$COOH, —CH$_2$CH(CH$_3$)COOH, —CH$_2$CH(C$_2$H$_5$)CH$_2$COOH, —CH$_2$CH(CH$_3$)CH(CH$_3$)CH$_2$COOH and the like. The —CH$_2$CH(CH$_3$)COOH radical is a preferred carboxyalkyl radical.

Examples of carboxythioalkyl radicals include but are not limited to —CH$_2$CH$_2$SCOOH, —(CH$_2$)$_3$SCOOH, —CH$_2$CH(CH$_3$)SCH$_2$COOH, —CH$_2$CH$_2$SCH$_2$COOH, —CH$_2$CH(C$_2$H$_5$)SCH$_2$COOH, and the like. The —CH$_2$CH$_2$SCH$_2$COOH radical is a preferred carboxythioalkyl radical.

Examples of emollients and moisturizers which may be used in this invention include straight, branched or cyclic hydroxy compounds such as alcohols containing 1 to 30 carbon atoms; straight, branched or cyclic carboxylic acids containing 1 to 31 carbon atoms; acid esters containing C$_1$ to C$_{30}$ carboxylic acids esterfied with C$_1$ to C$_{30}$ alcohols; alcohol ethers containing 1 to 30 carbon atoms; alkanes of the formula H—(CH$_2$)n—H wherein n is 5 to 30; and siloxanes. Examples of such functional materials include 2-ethylhexyl oxystearate; arachidyl propionate; 2-ethylhexyl adipate; isopropyl myristate; ethanol; stearyl alcohol; propylene glycol; propionic acid; stearic acid; polyoxypropylene cetyl alcohol; polyoxypropylene lanolin alcohol; Carbowax ® 300; petroleum Jelly; mineral oil; aliphatic hydrocarbons such as mineral spirits; lanolin and lanolin derivatives such as acetylated lanolin and isopropyl lanolate; hexamethyldisiloxane; cyclic polydimethylsiloxane; linear polydimethylsiloxane; polyphenylmethylsiloxane; and polydimethyl/trimethylsiloxane. Other phenyl, ethyl and vinyl substituted polysiloxanes may also be included.

In order to illustrate the durability enhancement of the siloxanes, durability enhancement data was collected for a variety of emollients. A soap washing test procedure was used in order to measure the influence of the silicones on the durability of the various emollients. The emollients considered were mineral oil, mink oil, lanolin oil, and petrolatum. The test procedure was used to measure silicone substantivity on human skin. The method was based on Attenuated Total Reflectance/Fourier Transform Infrared Spectrophotometric (ATR/FTIR) analysis in which prism skin studies were conducted and analyzed based on the reflection of energy at the interface. Instrumentation included a NICOLET Model 20DX FTIR system and a HARRICK Scientific Skin Analyzer. The ATR studies involved contact of the skin sample and prism. A hydration procedure was employed in order to increase the softness and flexibility of the skin surface which resulted in a less variable contact between the skin and prism. This hydration procedure included placing a water soaked towel against the skin test site for one minute prior to actual spectra collection. A skin test site selected was an area of about eighty square centimeters, and about ten to twelve milligrams of each solution tested was applied to the skin test site area in the form of a thin film using a small paint brush. From the data collected, it was possible to calculate percentages of ingredients remaining on the skin following various soap wash sequences. The soap employed was a 0.5 weight percent solution of IVORY ® bar soap and a soap rub was two passes over the test area with the soap solution cupped in the palm of the hand. One soap wash procedure included fifteen soap rubs and ten rinse rubs under cool running tap water. The test site was the volar forearm. The test solutions were applied to the skin test site on the forearm in the form of a mixture of the various silicones and emollient dissolved in a volatile silicone fluid of low viscosity such as polydimethylcyclosiloxane. This siloxane is a mixture of tetramers and pentamers having a viscosity of about 2.5 centistokes measured at twenty-five degrees Centigrade. The solution contained five to ten percent by weight of the mixture in the solvent. The solvent was allowed to evaporate from the volar forearm region for fifteen to thirty minutes prior to the institution of the measurement procedures. The site was hydrated and initial spectrum was collected. The data included tests conducted with and without the presence of the various silicones in the test mixture and at least two test runs were conducted for each mixture.

EXAMPLE I

In a simplified test procedure, a test area on the forearm was marked and the test area was washed with the soap solution using fifteen rubs followed by rinsing with ten rubs under coal running water. Excess moisture was blotted from the forearm with a towel. After one minute the skin was hydrated for one minute using a towel saturated with water which was held loosely over the test area. Excess moisture was blotted and at the end of thirty seconds a background scan was conducted. The test mixture was applied to the skin test area and the solvent allowed to evaporate. The skin was again hydrated for one minute and excess moisture was blotted off. After thirty seconds a scan was conducted of the test area which represented an Initial Condition. The test area was washed with the soap solution using fifteen rubs followed by ten rinses and the excess moisture was blotted off. After one minute the skin was hydrated for one minute; blotted and at the end of thirty seconds a scan was run of the test area which represented a First Soap Wash Condition. Similar steps were repeated for second, third, and fourth soap wash conditions. Baselines for infrared bands were defined and band heights were measured. The percent ingredient remaining on the skin was calculated using this data.

The following tables set forth the results of the foregoing procedure and illustrate the durability enhancement of various emollients with certain functional silicones. The tables indicate that the functional silicones enhance emollient durability and provide a viable alternative to dry, chapped and rough skin which results when the emollients are removed by ordinary washing. The siloxanes are soap wash resistant and have shown minimal or no dermal irritation. The carboxyfunctional siloxane possesses the least dermal irritation of the siloxanes tested. The functional silicones in the tables conform to the formula $Me_3SiO(Me_2SiO)_x(MeRSiO)_ySiMe_3$ in which Me is methyl and R is the functional group. Specifics of the R group and values of the integers x and y are set forth in the tables. Unless otherwise indicated mixtures of emollient and silicones were in a ratio of four to one and the mixtures were delivered in the form of mixtures including a volatile cyclic siloxane.

Mixtures may contain other adjuvants such as perfumes, fragrances and preservatives provided the addition of the adjuvant would not materially affect the basic and novel characteristics of the composition and would not materially change its fundamental characteristics.

TABLE I

EMOLLIENTS - NO SILICONE PERCENT REMAINING

| Test Condition | Mink Oil | Lanolin Oil | Mineral Oil | Petrolatum |
|---|---|---|---|---|
| Initial | 100 | 100 | 100 | 100 |
| 1st wash | 32 | 33 | 32 | 44 |
| 2nd wash | 19 | 21 | 16 | 34 |
| 3rd wash | 14 | 15 | 6 | 19 |
| 4th wash | — | — | 4 | 16 |
| 5th wash | — | — | 2 | 13 |

TABLE II

COMPOUNDS USED AMINE AND AMIDE FUNCTIONAL SILICONES

| Silicone | R-Group | M % R | x | y | x/y |
|---|---|---|---|---|---|
| A | $iBuNH(CH_2)_2NH_2$ | 1 | 97 | 1 | 91/1 |
| B | $iBuNH(CH_2)_2NH_2$ | 2 | 96 | 2 | 48/1 |
| C | $iBuNH(CH_2)_2NH_2$ | 5 | 188 | 10 | 19/1 |
| D | $iBuNH(CH_2)_2NH_2$ | 0.7 | 296 | 2 | 148/1 |
| E | $iBuNH(CH_2)_2NH_2$ | 0.5 | 445.8 | 2.2 | 203/1 |
| F | $iBuNH(CH_2)_2NH_2$ | 1.7 | 440.4 | 7.6 | 58/1 |
| G | $iBuNH(CH_2)_2NH_2$ | 0.25 | 796 | 2 | 398/1 |
| H | $iBuNH(CH_2)_2NHCOCH_3$ | 2 | 96 | 2 | 48/1 |

TABLE III

PERCENT REMAINING MINERAL OIL AND SILICONES

| Test Condition | SILICONES | | | | | | | |
|---|---|---|---|---|---|---|---|---|
| | H | A | B | C | D | E | F | G |
| INITIAL | 100 | 100 | 100 | 100 | 100 | 100 | 100 | 100 |
| 1st wash | 46 | 56 | 53 | 47 | 46 | 46 | 50 | 52 |
| 2nd wash | 28 | 38 | 35 | 35 | 40 | 32 | 34 | 41 |
| 3rd wash | 22 | 32 | 28 | 30 | 32 | 32 | 28 | 32 |
| 4th wash | 20 | 30 | 24 | 27 | 26 | 26 | 21 | 30 |
| 5th wash | 17 | 25 | 20 | 24 | 22 | 25 | 20 | 19 |

TABLE IV

PERCENT REMAINING MINERAL OIL AND SILICONES

| Test Condition | Polydimethylsiloxane (1) | | | H | Average A-G |
|---|---|---|---|---|---|
| | 100 DP | 550 DP | 6800 DP | | |
| INITIAL | 100 | 100 | 100 | 100 | 100 |
| 1st wash | 35 | 35 | 45 | 46 | 50 |
| 2nd wash | 24 | 20 | 37 | 28 | 36 |
| 3rd wash | 20 | 18 | 31 | 22 | 31 |
| 4th wash | 18 | 16 | 27 | 20 | 26 |
| 5th wash | 14 | — | 24 | 17 | 22 |

(1): 100 DP is 350 centistoke fluid.
550 DP is hydroxyendblocked fluid with partial trimethylcapping.
6800 DP is a siloxane gum.

TABLE V

| Sample Number | Polymer Description | % Mineral Oil Remaining | | | | | |
|---|---|---|---|---|---|---|---|
| | | Initial Condition | 1st Wash | 2nd Wash | 3rd Wash | 4th Wash | 5th Wash |
| 1 | No Silicone | 100 | 32 | 16 | 6 | 4 | 2 |
| 2 | H | 100 | 56 | 34 | 25 | 20 | 14 |
| 3 | A | 100 | 40 | 26 | 18 | 16 | 14 |
| 4 | B | 100 | 52 | 27 | 18 | 19 | 13 |
| 5 | C | 100 | 40 | 28 | 25 | 18 | 14 |
| 6 | D | 100 | 58 | 36 | 30 | 17 | 8 |
| 7 | E | 100 | 66 | 41 | 34 | 26 | 24 |
| 8 | F | 100 | 58 | 37 | 28 | 17 | 15 |
| 9 | G | 100 | 33 | 30 | 18 | 20 | 5 |

TABLE VI

Compounds Used Carboxyfunctional Silicones

| Reference | R-Group | M % R | x | y | x/y |
|---|---|---|---|---|---|
| J | iPr COOH | 3 | 201.7 | 6.3 | 32/1 |
| K | iPr COOH | 0.7 | 296 | 2 | 148/1 |
| L | iPr COOH | 3.3 | 288 | 10 | 29/1 |
| M | iPr COOH | 15 | 253 | 45 | 6/1 |

TABLE VII

Percent Remaining Mineral Oil and Silicone

| Test Condition | J | K | L |
|---|---|---|---|
| INITIAL | 100 | 100 | 100 |
| 1st Wash | 44 | 42 | 29 |
| 2nd Wash | 30 | 33 | 19 |
| 3rd Wash | 24 | 28 | 14 |
| 4th Wash | 21 | 26 | 13 |
| 5th Wash | 19 | 22 | 15 |

TABLE VIII

Mineral Oil and Silicone Percent Silicone Remaining

| Test Condition | Polydimethylsiloxane | | | | A-G Amino Avg. | J-K Carboxylic Acid Avg. |
|---|---|---|---|---|---|---|
| | 100 DP | 550 DP | 6800 DP | H | | |
| INITIAL | 100 | 100 | 100 | 100 | 100 | 100 |
| 1st Wash | 35 | 35 | 45 | 46 | 50 | 43 |
| 2nd Wash | 24 | 20 | 37 | 28 | 36 | 32 |
| 3rd Wash | 20 | 18 | 31 | 22 | 31 | 26 |

TABLE VIII-continued

| | Mineral Oil and Silicone Percent Silicone Remaining | | | | |
|---|---|---|---|---|---|
| | Polydimethylsiloxane | | | A-G | J-K |
| Test Condition | 100 DP | 550 DP | 6800 DP | H Amino Avg. | Carboxylic Acid Avg. |
| 4th Wash | 18 | 16 | 27 | 20 26 | 24 |
| 5th Wash | 14 | — | 24 | 17 22 | 20 |

TABLE IX

| | Mineral Oil and Silicone % Mineral Oil Remaining | | | |
|---|---|---|---|---|
| Test Condition | No Silicone | J | K | L |
| INITIAL | 100 | 100 | 100 | 100 |
| 1st Wash | 32 | 47 | 52 | 32 |
| 2nd Wash | 16 | 30 | 36 | 20 |
| 3rd Wash | 6 | 19 | 24 | 13 |
| 4th Wash | 4 | 13 | 22 | 6 |
| 5th Wash | 2 | 8 | 12 | 4 |

TABLE X

| | Two to One Mink Oil and Silicone % Mink Oil Remaining | | | |
|---|---|---|---|---|
| Test Condition | No Silicone | Carboxylic Acid | | |
| | | J | K | L |
| INITIAL | 100 | 100 | 100 | 100 |
| 1st Wash | 32 | 46 | 45 | 30 |
| 2nd Wash | 19 | 28 | 28 | 17 |
| 3rd Wash | 14 | 26 | 25 | 10 |

It has been discovered that human skin can be treated to enhance the ability of skin in the absorption and retention of moisture in order to retard skin moisture loss by applying to skin an organosilicon compound exhibiting humectant-like characteristics. This organosilicon compound is a carboxylic acid salt functional polysiloxane having the formula

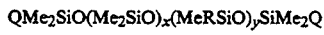

$QMe_2SiO(Me_2SiO)_x(MeRSiO)_ySiMe_2Q$ in which Me is methyl; Q is R, Me or OH; x has a value of 1–1000; y has a value of 1–100; R is a carboxylic acid salt group having the formula —R'COOM in which R' is a divalent organic group having from 2–10 carbon atoms; and M is a cation selected from the group consisting of $Na^+$, $K^+$ and $Li^+$.

R' is one of an alkylene, alkylenearylene or sulfur containing alkylene group. Such R' group can be $-CH_2CH_2-$, $-CH_2CH_2CH_2-$, $-CH_2CH_2CH_2CH_2-$, $-CH_2CH(CH_3)CH_2-$, $-(CH_2)_2C_6H_4-$, $-CH_2CH_2S-$, $-CH_2CH_2SCH_2-$, $-CH_2CH_2CH_2SCH_2-$, or $-CH_2CH(CH_3)CH_2S-$ for example.

It has also been discovered that human skin can be treated to reduce the transepidermal water loss of skin in order to enhance skin softness by applying to skin an occlusive film forming organosilicon compound which is either the carboxylic acid salt functional polysiloxane shown above or a carboxyfunctional polysiloxane having the formula

$QMe_2SiO(Me_2SiO)_x(MeRSiO)_ySiMe_2Q$ wherein Me is methyl; Q is R, Me or OH; x has a value of 1–1000; y has a value of 1–100; and R is a carboxyfunctional substituent selected from the group consisting of carboxyalkyl radicals and carboxythioalkyl radicals. Most preferably x is less than about three hundred and y is less than about ten.

In this embodiment, the occlusive film forming organosilicon compound can be applied to the skin as a formulated product or it can be applied without a solvent or "neat". The average reduction in the rate of transepidermal water loss has been found to be about twenty percent.

While U.S. Pat. No. 4,844,888 issued Jul. 4, 1989 teaches the application to the skin of certain compositions said to contain carboxy- or carboxy-ester-functional polysiloxanes, the composition which is applied to the skin is actually a partially covalently crosslinked reaction product of two different types of siloxanes. Thus in accordance with the '888 patent the hydroxy or alkoxy groups of an aminofunctional polysiloxane condense with each other. This is followed by a chemical reaction between the carboxyl groups of a carboxy-or carboxy-ester-functional polysiloxane and the primary amine groups of the aminofunctional polysiloxane. For this reason, the prior art does not teach applying to skin the carboxyfunctional siloxanes of the present invention or their carboxylic acid salts.

The following examples illustrate these concepts in accordance with the present invention.

EXAMPLE II

A method was developed to measure the humectant-/hygroscopic properties of materials as a function of relative humidities. The method was used to generate a screen of materials and correlate humectant ranking to glycerine a well known humectant.

Five constant humidity chambers were constructed as follows:

1. 0% R.H. using $CASO_4$ (Drierite)
2. 35% R.H. using $CaCl_2$ saturated in $H_2O$
3. 52% R.H. using $Na_2Cr_2O_7$ saturated in $H_2O$
4. 66% R.H. using $NANO_2$ saturated in $H_2O$
5. 86% R.H. using $KHSO_4$ saturated in $H_2O$ The actual humidities of the chambers were not measured and a constant temperature was not maintained. A glycerine sample was included as a control with each new set of unknowns to account for any variation in temperature or humidity. The number of samples tested varied between four and eight. About five grams of each sample were weighed into weighed metal or plastic dishes and the weights were recorded. The samples were placed in the 0% R.H. chamber and allowed to equilibrate to constant weight. The time to reach constant weight was 18–20 days. After equilibration at 0% R.H., the dry weight of the samples was recorded and the samples were placed in the 35% R.H. chamber. This procedure was repeated until the samples had been equilibrated in all of the chambers.

Two calculation modes were used for the data.

Weight % Increase at $X$ % R.H. = (Mode I)

$$\frac{(Gm \text{ at } X\% \ R.H.)(Gm \text{ at } 0\% \ R.H.)}{(Gm \text{ at } 0\% \ R.H.)} \times 100$$

Mole $H_2O$/Mole $R$ at $X$ % R.H. = (Mode II)

$$\frac{\frac{(Gm \text{ at } 0\% \ R.H.)(\text{wt } \% \text{ inc. at } X\% \ R.H.)}{(100 \times 18)}}{\frac{(Gm \text{ at } 0\% \ R.H.)(\text{Mole } R/\text{Mole Sample})}{M. \ Wt. \text{ of Sample}}}$$

where $X\%$ R.H. = 35%, 52%, 66%, 86% R.H. and R is an active group such as OH for glycerine or COONa for the carboxylate salts.

The composition of the carboxylic acid and metal carboxylate salt functional silicones are set forth in Table XI.

TABLE XI

| | Me₃SiO[Me₂SiO]ₓ[MeRSiO]ᵧSiMe₃ | | | |
|---|---|---|---|---|
| Material | R Group | M % R[a] | x | y | DP[b] |
| 1 | iPrCOOH | 10 | 88 | 10 | 100 |
| 2 | EtSCH₂COOH | 15 | 83 | 15 | 100 |
| 3 | EtSCH₂COONa | 1 | 146.5 | 1.5 | 150 |
| 4 | EtSCH₂COONa | 15 | 125.5 | 22.5 | 150 |
| 5 | EtSCH₂COOK | 1 | 97 | 1 | 100 |
| 6 | EtSCH₂COOK | 8 | 136 | 12 | 150 |
| 7 | EtSCH₂COOK | 15 | 83 | 15 | 100 |

[a]mole percent of R group.
[b]degree of polymerization.

Weight % Increase date was determined as a function of % R.H. and is set forth in the following table.

TABLE XII

| | | | WEIGHT % INCREASE | | | |
|---|---|---|---|---|---|---|
| Material | R Group | M % R | 35% R.H. | 52% R.H. | 66% R.H. | 86% R.H. |
| 1 | iPrCOOH | 10 | — | — | 0 | 0 |
| 2 | EtSCH₂COOH | 15 | — | — | 0.4 | 0.7 |
| 3 | EtSCH₂COONa | 1 | 0 | 0 | 0.3 | 0.7 |
| 4 | EtSCH₂COONa | 15 | 0.3 | 4.5 | 7.7 | 17.4 |
| 5 | EtSCH₂COOK | 1 | 0 | 0.3 | 0.4 | 0.7 |
| 6 | EtSCH₂COOK | 8 | 0.2 | 3.4 | 4.7 | 8.8 |
| 7 | EtSCH₂COOK | 15 | 0.6 | 5.0 | 7.1 | 14.6 |

The carboxylic acid functional polymers 1 and 2 exhibited minimal humectancy properties. Conversion of the acid to a metal carboxylate salt dramatically increased the hygroscopicity of these polymers. The weight % Increase at each relative humidity correlates with the M%R group in the polymer. The potassium salt is more effective at lower relative humidities than the sodium salt. However the sodium salts are more active at higher relative humidities. A comparison to glycerine was conducted based upon the level of active sites in the molecule. This data for mole ratio of H₂O/R-Group is set forth in Table XIII.

TABLE XIII

| | | | MOLE H₂O/ MOLE R GROUP | | | |
|---|---|---|---|---|---|---|
| Material | Group | M % R | 35% R.H. | 52% R.H. | 66% R.H. | 86% R.H. |
| Glycerine | OH | 3 | 0.2 | 0.5 | 0.8 | 1.8 |
| 3 | EtSCH₂COONa | 1 | 0 | 0 | 1.1 | 2.7 |
| 4 | EtSCH₂COONa | 15 | 0.1 | 1.4 | 2.4 | 5.4 |
| 5 | EtSCH₂COOK | 1 | 0 | 1.3 | 1.7 | 2.8 |
| 6 | EtSCH₂COOK | 8 | 0.1 | 1.9 | 2.6 | 4.9 |
| 7 | EtSCH₂COOK | 15 | 0.2 | 1.6 | 2.3 | 4.7 |

Based upon the number of active sites in the molecule, the metal carboxylate salt functional polymers demonstrated more efficient humectant properties than glycerine especially at 52% R.H. One disadvantage of glycerine as a humectant in skin care applications is its limited effectiveness at low relative humidities. These metal carboxylate salt functional polymers overcome this limitation and provide the inherent aesthetic benefits of silicone polymers.

No standard method has been accepted in the skin care industry to define the moisturization properties of a particular ingredient. Different properties of moisturizers can be measured such as humectancy and occlusivity. A reduction in the loss of water from the skin surface or occlusivity contributes to increased softness and flexibility of skin. The occlusive properties of an ingredient can be measured using a Servo-Med Evaporimeter to determine the reduction in transepidermal water loss (% TWL) caused by the ingredient relative to untreated skin. Data was collected for silicone polymers applied "neat" to skin and the results were compared to a well known occlusive agent petrolatum.

EXAMPLE III

Three 4.25 cm diameter circles were drawn on the left underarm of a volunteer with the sites labelled 1, 2, and 3 from elbow to wrist. The volunteer was required to remain in a controlled humidity room for 30 minutes prior to the start of measurement. Background data of untreated skin (WE)₀ was collected for each site by placing the evaporimeter probe perpendicular to the arm and readings were recorded for two minutes at each site. Data collection was repeated for each site until constant values for each site were recorded. A weighed quantity of material sufficient to form a film was applied to each site and spread to a uniform thin film using the flat edge of a glass medicine dropper. Treated site data (WE)₁ was collected at 30 minute intervals beginning 30 minutes after the initial application. Data was collected for 120-150 minutes and the constant values averaged. % TWL was calculated using the following equation:

$$\% \ TWL \ \text{Reduction} = \frac{(WE)_1 - (WE)_0}{(WE)_0} \times 100$$

The siloxane polymers used in Example III are set forth in Table XIV.

TABLE XIV

| Material | Description | R Group | M % R | x | y | DP |
|---|---|---|---|---|---|---|
| 1 | 1000 cs PDMS* | — | — | 213 | — | 215 |
| 2 | 30000 cs PDMS* | — | — | 648 | — | 650 |
| 3 | 300000 cs PDMS* | — | — | 1113.0 | — | 1115 |
| 4 | — | iBuNH(CH₂)₂NH₂ | 0.7 | 296.0 | 2.0 | 300 |
| 5 | — | iBuNH(CH₂)₂NH₂ | 0.5 | 445.8 | 2.2 | 450 |
| 6 | — | iPrCOOH | 3.0 | 201.7 | 6.3 | 210 |
| 7 | — | iPrCOOH | 0.7 | 296.0 | 2.0 | 300 |

*PDMS = polydimethylsiloxane fluid.

All data was collected over a loading range of 5-23 mg/14.2 cm². Table XV shows the range of % TWL Reduction observed for this loading range and a calculated average for several tests of each material.

TABLE XV

| Material Description | Material | % T W L Reduction Average |
|---|---|---|
| Petrolatum | — | 57 |
| Glycerine | — | 8 |
| 1000 cs PDMS | 1 | 4 |
| 30000 cs PDMS | 2 | 16 |
| 300000 cs PDMS | 3 | 29 |

TABLE XV-continued

| Material Description | Material | % T W L Reduction Average |
|---|---|---|
| 300 DP 0.7% Amino | 4 | 15 |
| 450 DP 0.5% Amino | 5 | 14 |
| 210 DP 3.0 M % COOH | 6 | 20 |
| 300 DP 0.7 M % COOH | 7 | 40 |

The carboxylic acid functional materials demonstrated an unexpected reduction of % TWL relative to polymer DP. The amino functional polymers show some benefit over PDMS but the carboxylic acid functional polymers are more efficient at reducing TWL. Petrolatum is an effective occlusive agent but the carboxylic acid functional polymer has better aesthetics than petrolatum. The active moisturizing and occlusive agent is believed to be the metal carboxylate salt formed in situ.

Metal carboxylate salt functional silicone polymers have been shown to exhibit humectant and occlusive properties. The humectancy of the sodium and potassium salts is greater than glycerine on a mole ratio basis of water to active site. These salts are more active at lower relative humidities than glycerine. In vivo evaluation of the carboxylic acid functional polymers and their metal carboxylate salts demonstrated an unexpected reduction in % TWL relative to the polymer DP.

It will be apparent from the foregoing that many other variations and modifications may be made in the compounds, compositions and methods described herein without departing substantially from the essential features and concepts of the present invention. Accordingly, it should be clearly understood that the forms of the invention described herein are exemplary only and are not intended as limitations on the scope of the present invention as defined in the appended claims.

That which is claimed is:

1. A method of treating human skin comprising applying to skin an organosilicon compound exhibiting humectant-like characteristics, the organosilicon compound being a carboxylic acid salt functional polysiloxane having the formula

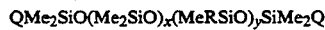

in which Me is methyl; Q is R, Me or OH; x has a value of 1–1000; y has a value of 1–100; R is a carboxylic acid salt group having the formula —R'COOM in which R' is a divalent organic group having from 2–10 carbon atoms; and M is a cation selected from the group consisting of Na+, K+ and Li+.

2. The method of claim 1 in which R' is selected from the group consisting of alkylene, alkylenearylene and sulfur containing alkylene groups.

3. The method of claim 2 in which R' is —CH2CH2—, —CH2CH2CH2—, —CH2CH2CH2CH2—, —CH2CH(CH3)CH2—, —(CH2)2C6H4—, —CH2CH2S—, —CH2CH2SCH2—, —CH2CH2CH2SCH2—, or —CH2CH(CH3)CH2S—.

4. The method of claim 3 in which R' is —CH2CH2SCH2—.

5. The method of claim 4 in which M is Na+.

6. The method of claim 4 in which M is K+.

7. A method of treating human skin comprising applying to skin an occlusive film forming organosilicon compound, the organosilicon compound being selected from the group consisting of a carboxyfunctional polysiloxane having the formula

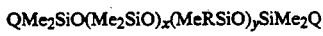

wherein Me is methyl; Q is R, Me or OH; x has a value of 1–1000; y has a value of 1–100; R is a carboxyfunctional substituent selected from the group consisting of carboxyalkyl radicals and carboxythioalkyl radicals; and a carboxylic acid salt functional polysiloxane having the formula

in which Me is methyl; Q is R, Me or OH; x has a value of 1–1000; y has a value of 1–100; R is a carboxylic acid salt group having the formula —R'COOM in which R' is a divalent organic group having from 2–10 carbon atoms; and M is a cation selected from the group consisting of Na+, K+ and Li+.

8. The method of claim 7 wherein the occlusive film forming organosilicon compound is applied to the skin as a formulated product.

9. The method of claim 7 wherein the occlusive film forming organosilicon compound is applied to the skin as a formulated product.

10. The method of claim 7 wherein R is —CH(CH3)2COOH.

11. The method of claim 7 wherein x is less than about three hundred and y is less than about ten.

12. The method of claim 7 wherein the average reduction in the rate of transepidermal water loss is at least about twenty percent.

13. The method of claim 7 in which R' is selected from the group consisting of alkylene, alkylenearylene and sulfur containing alkylene groups.

14. The method of claim 13 in which R' is —CH2CH2—, —CH2CH2CH2—, —CH2CH2CH2CH2—, —CH2CH(CH3)CH2—, —(CH2)2C6H4—, —CH2CH2S—, —CH2CH2SCH2—, —CH2CH2CH2SCH2—, or —CH2CH(CH3)CH2S—.

15. The method of claim 14 in which R' is —CH2CH2SCH2—.

16. The method of claim 15 in which M is Na+.

17. The method of claim 15 in which M is K+.

* * * * *